(12) United States Patent
Mandeau et al.

(10) Patent No.: US 8,999,402 B2
(45) Date of Patent: Apr. 7, 2015

(54) HYPOALLERGENIC DERMATOLOGICAL COMPOSITION

(75) Inventors: Anne Mandeau, Toulouse (FR); Bernard Fabre, Belberaud (FR); Valérie Teysseyre, Montbrun Lauragais (FR); Jean-François Boe, Ramonville Saint Agne (FR); Véronique Crebassa Trigueros, Toulouse (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 999 days.

(21) Appl. No.: 13/129,242

(22) PCT Filed: Sep. 15, 2009

(86) PCT No.: PCT/EP2009/061971
§ 371 (c)(1),
(2), (4) Date: May 13, 2011

(87) PCT Pub. No.: WO2010/054878
PCT Pub. Date: May 20, 2010

(65) Prior Publication Data
US 2011/0217399 A1    Sep. 8, 2011

(30) Foreign Application Priority Data

Nov. 14, 2008    (FR) ..................... 08 57755

(51) Int. Cl.
  *A01N 65/00*    (2009.01)
  *A61K 8/97*    (2006.01)
  *A61K 8/64*    (2006.01)
  *A61Q 19/00*    (2006.01)

(52) U.S. Cl.
  CPC ... *A61K 8/97* (2013.01); *A61K 8/64* (2013.01); *A61Q 19/00* (2013.01); *A61K 2800/72* (2013.01)

(58) Field of Classification Search
  None
  See application file for complete search history.

(56) References Cited

U.S. PATENT DOCUMENTS

| 4,382,961 A | 5/1983 | Nedeczky et al. |
| 5,612,074 A | 3/1997 | Leach |
| 2008/0089957 A1 | 4/2008 | Chen et al. |

FOREIGN PATENT DOCUMENTS

| EP | 1764898 A1 | 9/2006 |
| FR | 2487674 A1 | 2/1982 |
| FR | 1474159 A | 4/2011 |
| JP | 2000-143524 A | 5/2000 |
| JP | 2004-115503 A | 4/2004 |
| WO | WO 95/26183 A1 | 10/1995 |
| WO | WO 2003/066073 A3 | 6/2003 |

OTHER PUBLICATIONS

Palosue et al., "Rye γ-70 and γ-35 secalins and barley γ-3 hordein cross-react with ω-5 gliadin, a major allergen in wheat-dependent, exercise-induced anaphylaxis," Clinical and Experimental Allergy, 2001, vol. 31, pp. 456-473.

Paris et al., "Classe des Monocotyledones," Graminées, Matière Médicale, Collection de Précis de Pharmacie Sous La Direction de M.-M. Janot, 2nd Edition. pp. 16-17, (1981).

Pecquet et al., "Hydrolysats de protéines du blé:nouveaux allergènes, (New allergens in hydrolysates of wheat proteins)," Revue Francaise D'Allergologie et D'Immunologie Clinique, vol. 43. pp. 21-23.

Varjonen et al., "Skin-prick test and RAST responses to cereals in children with a topic dermatitis. Characterization of IgE-binding components in wheat and oats by an immunoblotting method," Clinical and Experimental Allergy, 1995, vol. 25. pp. 1100-1107.

Bahraminejad et al., "Analysis of the Antimicrobial Activity of Flavonoids and Saponins Isolated from the Shoots of Oats (*Avena sativa* L.)", Journal of Phytopathology, vol. 156, No. 1, pp. 1-7, Jan. 2008.

Baumgertel et al., "Purification and Characterization of a Flavonol 3-O-β- Heterodisaccharidase from the Dried Herb of Fagopyrum Esculentum Moench", Phytochemistry, vol. 64, No. 2, pp. 411-418, (2003).

Fowler et al., "Active Naturals Have a Key Role in Atopic Dermatitis", Seminars in Cutaneous Medicine and Surgery, vol. 27, No. 3, pp. 8-10, Sep. 1, 2006.

Hänsel et al., "Hagers Handbuch der Pharmazeutischen Praxis 4 Drogen A-D". 1992, XP002535813.

Hänsel et al., "Hagers Handbuch der Pharmazeutischen Praxis 5 Drogen E-O", 1993, XP002535812.

Hänsel et al., "Hagers Handbuch der Pharmazeutischen Praxis 4 Drogen A-D", 1992, XP002532360.

Hinneburg et al., Database Biosis, "Antioxidant and Photoprotective Properties of an Extract from Buckwheat Herb (*Fagopyrum exculentum* Moench)", vol. 61, No. 3, pp. 237-240, Mar. 2006, XP002535814. Accession No. PREV200600435277.

Hinneburg et al., Database Biosis, "Influence of Extraction Parameters on the Phytochemical Characteristics of Extracts from Buckwheat (*Fagopyrum esculentum*) Herb", vol. 53, No. 1, pp. 3-7, Jan. 12, 2005, XP002535815. Accession PREV200500142560.

Ihme et al., "Leg Oedema Protection From a Buckwheat Herb Tea in Patients with Chronic Venous Insufficiency: A Single-Centre, Randomised, Double-Blind, Placebo-Controlled Clinical Trial", European Journal of Clinical Pharmacology, vol. 50, No. 6, pp. 443-447, Jan. 1, 1996, XP001007946.

International Search Report dated Jun. 17, 2010 for Application No. PCT/EP2009/061971.

Pierre et al., "Avoine", Internet Article, pp. 1-5, Jan. 30, 2007, XP002532358.

*Primary Examiner* — Michael Meller
(74) *Attorney, Agent, or Firm* — Birch, Stewart, Kolasch & Birch, LLP

(57) ABSTRACT

The invention relates to a hypoallergenic dermatological composition comprising an extract of aerial part of cereal or pseudocereal, excluding the grains, for use in persons allergic to cereals.

1 Claim, 3 Drawing Sheets

HYPOALLERGENIC DERMATOLOGICAL COMPOSITION

Figure 1:
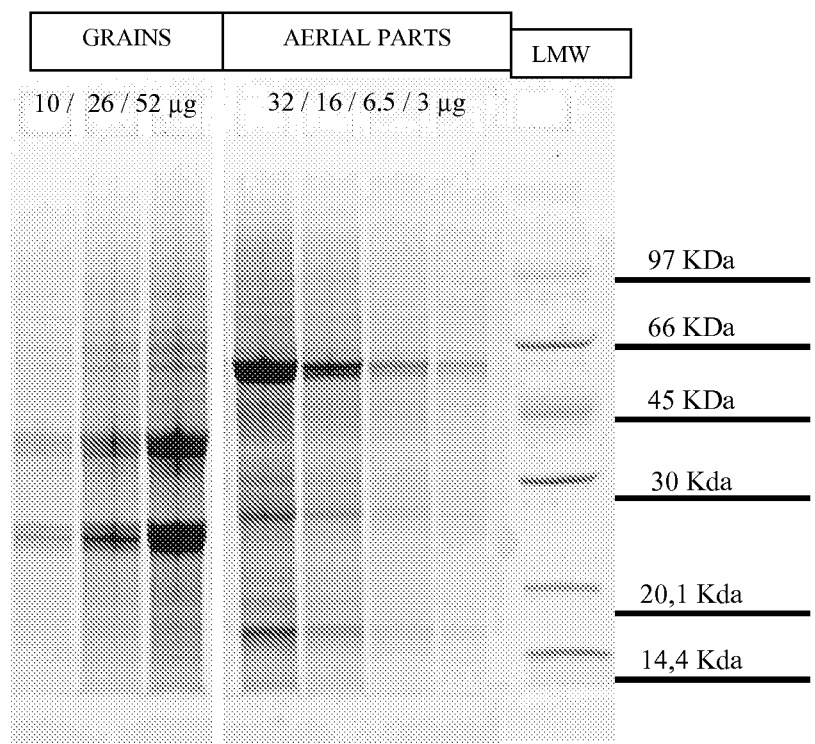

The present invention relates to allergies to cereals.

Within the meanings of the present invention, the cereals include Poaceae and pseudocereals.

The term <<cereals>> relates to Gramineae, the ripe <<grain>> (caryopsis) of which is used as a food, especially because of its high starch content (Paris R. R., Moyse H. Précis de matière médicale. II Pharmacognosie spéciale. Spermaphytes (continued): Angiospermes. Monocotylédones—Dicotylédones. Apétales et Diapétales. $2^{nd}$ Edition. Paris: Masson, 1981, p 16). The term <<cereal>> also relates specifically to the seed of these plants.

In botany, cereals belong to the Poaceae (or Gramineae) family.

Said Gramineae are generally grassy Monocots with a hollow stem between nodes (culm) carrying distichous leaves with an often split and ligule-containing sheath. Flowers are arranged in spikelets, and are most often grouped into compound spikes, or bunches called <<panicles>>. The flower is reduced to stamens and ovary: two leaf bracts or glumes protect the spikelet, and two lemmas, one of which being anterior, leaned, wrapping, often aristate, comes together with the flower. The three exserted stamens are oscillating, attached through their back. The ovary has 1 carpel with two feathery styles, intimately sealed to the ovule and developing into one particular fruit referred to as caryopsis; the abundant albumen is starchy.

This family includes approximately 700 genera and 12000 species.

Most grasses are used for food purposes (wheat, barley, rye, oats, sorghum, millet, corn, rice . . . ).

The cereal species most traditionally consumed are listed in Table 1 below.

TABLE 1

Main cereal species consumed, belonging to the Poaceae family

| Latin name | Vernacular name |
| --- | --- |
| *Avena abyssinica* Hochst. | |
| *Avena brevis* Roth | |
| *Avena nuda* L. | Nude oats |
| *Avena sativa* L. | |
| *Bromus mango* E. Desv. | |
| *Coix lacryma-jobi* var. *ma-yuen* (Rom. Caill.) Stapf | |
| *Dendrocalamus strictus* (Roxb.) Nees | |
| *Digitaria exilis* (Kippist) Stapf | |
| *Digitaria iburua* Stapf | |
| *Echinochloa esculenta* (A. Braun) H. Scholz | Japanese millet |
| *Eleusine coracana* subsp. *coracana* | red millet |
| *Eragrostis tef* (Zuccagni) Trotter | lovegrass |
| *Hordeum vulgare* subsp. *vulgare* | common barley |
| *Oryza glaberrima* Steud. | African rice |
| *Oryza sativa* L. | rice |
| *Panicum hirticaule* J. Presl | |
| *Panicum miliaceum* subsp. *miliaceum* | common millet |
| *Panicum sumatrense* Roth | |
| *Paspalum scrobiculatum* L. | |
| *Pennisetum glaucum* (L.) R. Br. | pearl millet |
| *Phalaris canariensis* L. | Canary grass |
| *Secale cereale* subsp. *cereale* | rye plant |
| *Secale strictum* subsp. *africanum* (Stapf) K. Hammer | |
| *Setaria italica* subsp. *italica* | Italian millet, foxtail millet, Chinese millet, Hungarian millet |
| *Setaria palmifolia* (J. Koenig) Stapf | |

TABLE 1-continued

Main cereal species consumed, belonging to the Poaceae family

| Latin name | Vernacular name |
| --- | --- |
| *Setaria pumila* subsp. *pumila* | little bristle grass |
| *Sorghum bicolor* subsp. *bicolor* | great millet sorghum |
| x*Triticosecale* spp. | triticale |
| *Triticum aestivum* subsp. *aestivum* | common wheat, wheat |
| *Triticum aestivum* subsp. *spelta* (L.) Thell. | spelt wheat |
| *Triticum aestivum* subsp. *sphaerococcum* (Percival) Mackey | |
| *Triticum monococcum* subsp. *monococcum* | small spelt, einkorn wheat |
| *Triticum timopheevii* subsp. *timopheevii* | |
| *Triticum turgidum* subsp. *carthlicum* (Nevski) A. Love & D. Love | Persian wheat |
| *Triticum turgidum* subsp. *durum* (Desf.) Husn. | durum wheat |
| *Triticum turgidum* subsp. *polonicum* (L.) Thell. | Polish wheat |
| *Triticum zhukovskyi* A. M. Menabde & Eritzjan | |
| *Urochloa deflexa* (Schumach.) H. Scholz | |
| *Urochloa ramosa* (L.) T. Q. Nguyen | |
| *Zizania palustris* L. | |
| *Zea mays* subsp. *mays* L. | corn |

Some grains from other botanical families are similar to cereals and referred to as pseudocereals. Examples of such species, which are related to cereals but are not part of the Poaceae family, also being consumed and which may be involved in food allergies include those listed in Table 2 below:

TABLE 2

Main species consumed related to cereals, not belonging to the Poaceae family

| Latin name | Vernacular name | Family |
| --- | --- | --- |
| *Amaranthus caudatus* L. | red hot cattail grain amaranth love-lies-bleeding foxtail | Amaranthaceae |
| *Amaranthus cruentus* L. | red amaranth | Amaranthaceae |
| *Amaranthus hypochondriacus* L. | | Amaranthaceae |
| *Chenopodium album* L. | white goosefoot | Chenopodiaceae |
| *Chenopodium berlandieri* subsp. *nuttalliae* (Saff.) H. D. Wilson & Heiser | | Chenopodiaceae |
| *Chenopodium pallidicaule* Aellen | | Chenopodiaceae |
| *Chenopodium quinoa* subsp. *quinoa* | quinoa, Peruvian rice | Chenopodiaceae |
| *Fagopyrum esculentum* Moench | common buckwheat, beech wheat | Polygonaceae |
| *Fagopyrum tataricum* (L.) Gaertn. | Tartarian buckwheat | Polygonaceae |
| *Helianthus annuus* L. | sunflower | Asteraceae |
| *Sesamum indicum* L. | sesame | Pedaliaceae |

The cereal and pseudocereal grains contain a large number of proteins: structural proteins, biologically functional proteins and spare proteins. Osborne (1907) has classified them according to their solubility:

Water-soluble albumins

Globulins soluble in saline solutions

Prolamines soluble in aqueous ethanol

Glutelins insoluble in the above solvents, partially soluble in urea or guanidin solutions.

Examples:

|  | Wheat | Oats | Barley | Corn |
|---|---|---|---|---|
| Albumins | Leukosines |  |  |  |
| Globulins | Edestines | Avenalins |  |  |
| Prolamines | Gliadins | Gliadins | Hordeins | Zeins |
| Glutelins | Glutenins | Avenins | Hordenines | Zeanins |

On the contrary, the protein content of aerial parts, in particular leaves, particularly consists of:
membrane proteins of chloroplasts (proteins often related to lipids and pigments)
soluble proteins of the chloroplast (stroma): RuBPCase Leaves of quinoa, sunflower, oats, barley, and *Zizania palustris*, young shoots of wheat, as well as sesame, rice, wheat and corn sprouts are already used in cosmetics. Young green barley shoots are for example used as an anti-ageing agent.

Also in the prior art it has been disclosed:
A leaf extract of Amaranthus used as an anti-inflammatory drug, in particular for treating atopic dermatitis (JP patent 2000143524).
A composition containing an extract of oat straw associated with a willowherb extract for treating inflammatory reactions of the skin for topical use (EP 1474159).
A cosmetic composition protected against oxidation by rice germ oil (EP1704898)
A cosmetic composition comprising a wheat sprout extract (WO9526183)
A cosmetic product having regenerative effects on skin containing an extract of sunflower stems (FR2487674)

Cereal flours, in particular wheat flour, are known to be responsible for baker's asthma and for allergic rhinitis through inhalation. The strongest IgE response was observed with albumins and globulins, which proteins are soluble in neutral solutions. However some studies have also demonstrated reactivity to proteins soluble in ethanol or in acidic medium (glutenins and gliadins). More recently, immunoblot studies have shown that major allergens in the neutral fractions of wheat and barley flour are situated in the low molecular weight range (around 20 kDa), in the serum of patients with baker's allergy.

When ingested, the cereals are sometimes responsible for coeliac disease and herpetic dermatitis. Several studies have shown the most involved antigen to be the gliadin fraction of ethanol-soluble proteins.

Despite the significance of cereals in human food, they are suspected to deteriorate atopic dermatitis conditions, especially in children. Likewise, immunology studies (essentially SPT tests—Skin Prick Test—and RAST—Radioallergosorbent Test) have led to identifying the proteins involved in wheat, oats, rye, barley, rice, millet and corn, and have demonstrated cross-reactions between wheat and barley or rye (Varjonen E, Vainio E, Kalimo K, Juntunen-Backman K, Savolainen J Skin-prick test and RAST responses to cereals in children with atopic dermatitis. Characterization of IgE-binding components in wheat and oats by an immunoblotting method. Clin Exp Allergy 1995, 25:1100-1107) (Palosuo K, Alenius H, Varjonen E, Kalkkinen N, Reunala T. Rye γ-70 and γ-35 secalins and barley γ-3 hordein cross-react with ω-5 gliadin, a major allergen in wheat-dependent, exercise-induced anaphylaxis. Clin Exp Allergy, 2001, 31:466-473). The least soluble proteins (gliadins and glutenins) seem to be involved when ingested cereals are the cause of atopic dermatitis. Many preliminary studies have shown that food hypersensitivity plays a significant role in children with atopic dermatitis, and that removing allergens from food results in clinical improvement.

Some instances of contact allergy have been reported with cosmetics based on extracts of cereal grains (essentially wheat proteins, whether hydrolyzed or non-hydrolyzed, but also sesame) in sensitized persons. Wheat protein hydrolysis, which could have been a solution to alleviate allergy problems, was shown to be on the contrary a lot more sensitizing, the structural changes induced by the hydrolysis revealing new antigen sites (Pecquet C, Laurière M. New allergens in hydrolysates of wheat proteins. Rev Fr Allerg Immunol Clin 2003, 43: 21-23).

It is thought that cereal grain proteins are to be avoided in allergic persons, both by oral and topical route, and especially in children.

There is therefore a need and a strong demand for cosmetics for persons who are sensitized or allergic to cereal grains.

Unexpectedly and surprisingly, the inventors have shown that a cosmetic composition comprising an extract of aerial part of cereals or pseudocereals harvested preferably before ear emergence, does not result in cross-reactions with those proteins responsible for cereal grain allergies.

The object of the present invention is therefore to provide an extract of aerial part(s) of cereal and/or pseudocereal, excluding the grains, for use in persons allergic to cereal grain proteins.

By the term aerial part of cereal and/or pseudocereal it is meant herein any part situated above the ground, excluding the grains.

Preferably, the <<aerial parts of cereals and/or pseudocereals>> include the leaves and/or stems and/or spikelets and/or flowers, excluding the grains.

Advantageously, the extract according to the invention is an extract of aerial part(s) of cereal and/or pseudocereal harvested before ear emergence.

Within the meanings of the present invention, the phrase <<aerial parts of cereal and/or pseudocereal harvested before ear emergence>> refers to the aerial parts of a cereal or pseudocereal harvested after germination (about 2 weeks to 2 months after germination) during the stem elongation stage up to, but excluding, the ear emergence.

Within the meanings of the present invention, the term <<stem elongation>> refers to the growth phase which corresponds to elongation of the stem and to the emergence of the forming ear, before blooming.

Preferably, the extract according to the invention is obtained from aerial part(s) of wheat, rice, barley or oats, more preferably oats.

An extract of aerial part(s) of oats advantageously used according to the invention in persons allergic to cereal grain proteins comprises 2 to 15% flavonoids and 0.2 to 2% A and B avenacosides, preferably 5 to 10% isovitexin-2"-O-arabinopyranoside and isoorientin-2"-O-arabinopyranoside flavonoids and/or less than 1 ppm proteins, preferably less than 0.5 ppm and even more preferably less than 0.3 ppm proteins.

The extract of aerial part(s) of oats used is characterized by its content in flavonoid and saponin of interest. The latter are analyzed by high pressure liquid chromatography, using either of two different methods, suitable for each type of compounds.

The amounts of these various molecules vary depending on extraction conditions. The main flavonoids are isovitexin-2"-O-arabinopyranoside and isoorientin-2"-O-arabinopyranoside. The A and B avenacosides are the main saponins. These are bisdesmosidic steroidal saponins.

Advantageously, the extract according to the invention is an extract of aerial part(s) of wheat, rice or oats harvested before ear emergence, and preferably of aerial part(s) of oats harvested before ear emergence.

Advantageously, the extract according to the invention is an extract obtained in an organic solvent.

The extract according to the invention can be prepared by extracting into an organic solvent aerial part(s) of a cereal or pseudocereal (about 2 weeks to 2 months after germination during the elongation stage up to, and excluding, the ear emergence) after drying and milling. In particular, an organic solvent selected from the group consisting of ketones, esters, C1 to C4 alcohols, and mixtures thereof in any miscible proportions, is used. Advantageously, an organic solvent selected from the group consisting of acetone, methyl ethyl ketone, methyl isobutyl ketone, ethyl acetate, a C1 to C4 alcohol, and a mixture thereof in any miscible proportion, is used.

The extraction is performed under stirring or statically.

The extraction is performed under reflux or at room temperature.

Advantageously, the extraction is performed at a plant/solvent ratio in the range of 1:7 to 1:20, preferably 1:8 to 1:12.

Preferably, the extraction is performed for a period of 30 minutes to 48 hours, most preferably 60 to 120 minutes.

The extraction can be repeated 2 or 3 times.

The pomace obtained from the extraction step is then separated from the extract by centrifugation or filtration, and the solution can be more or less concentrated until a dry matter is obtained.

A bleaching treatment can be carried out either by dilapidation through concentration, precipitation and filtration, or by admixing to the concentrated or non-concentrated extract solution an absorptive substrate such as activated carbon or an absorptive resin.

A substrate can be added at the drying step in weight ratios relative to the extracted dry matter in the range of 1 to 75%. The substrate can be a sugar such as maltodextrin, lactose, silica or any other cosmetologically acceptable substrate.

Advantageously, this extract results from extraction into acetone or acetone/water with up to 20% water. An acetone or acetone/water with up to 20% water extract contains the molecules of interest, flavonoids and saponins, and is highly depleted in proteins. In fact, the assay methods for the determination of proteins described in the European Pharmacopoeia are unsuccessful, and an electrophoretic migration on SDS-Page gel after precipitation from acetone and staining with Coomassie blue or silver nitrate shows the absence of a band indicating the presence of protein. Spotting a control on the same electrophoresis allows to assess the detection limit of protein as being about 1 ng, and this extract thus has a protein content below 1 ppm (based on the amount of extract spotted on the gel). Preferably, said protein content is less than 0.5 ppm and even more preferably less than 0.3 ppm proteins.

Another object of the present invention relates to the use of an extract of aerial part(s) of cereals and/or pseudocereals, excluding the grains, in persons allergic to cereal grain proteins.

Another object of the present invention relates to the use of an extract of aerial part(s) of cereals and/or pseudocereals, excluding the grains, for the preparation of a hypoallergenic dermatological composition, i.e. minimizing and/or preventing risks of allergic reactions in persons allergic to cereal grain proteins.

Another object of the present invention relates to the use of a cosmetic hypoallergenic composition comprising an extract of aerial part(s) of cereals and/or pseudocereals in persons allergic to cereal grain proteins.

The dermatological or cosmetic composition used according to the invention can particularly include additives and formulation aids, such as emulsifying agents, thickeners, gelling agents, water scavengers, spreading agents, stabilizers, dyes, perfumes and preservatives.

The dermatological or cosmetic composition used according to the invention further comprises usual dermatologically compatible excipients.

It may be prepared as a water-in-oil (W/O) or oil-in-water (O/W) emulsion, a multiple emulsion such as, for example, a water-in-oil-in-water (W/O/W) emulsion or an oil-in-water-in-oil (O/W/O) emulsion, or alternatively as a water-dispersion or oil-dispersion, a gel or an aerosol.

The dermatologically compatible excipients can be any excipient among those known to the person skilled in the art in order to obtain a composition for topical application in the form of a cream, a lotion, a gel, an ointment, an emulsion, a microemulsion, a spray, a shampoo, etc.

Advantageously, the dermatological or cosmetic composition used according to the invention comprises 0.1 to 10% of an extract of aerial part(s) of a cereal or pseudocereal, excluding the grains, by weight based on the total weight of the composition. Preferably, said composition comprises an extract of aerial part(s) of cereal according to the invention in an amount of between 0.1 and 5% by weight based on the total weight of the composition.

FIGURES

FIG. 1: Comparison of the profiles of total proteins from grains and young shoots of oats, by electrophoretic SDS-Page (12.5% polyacrylamide gel) staining with Coomassie blue.

Figure 2:
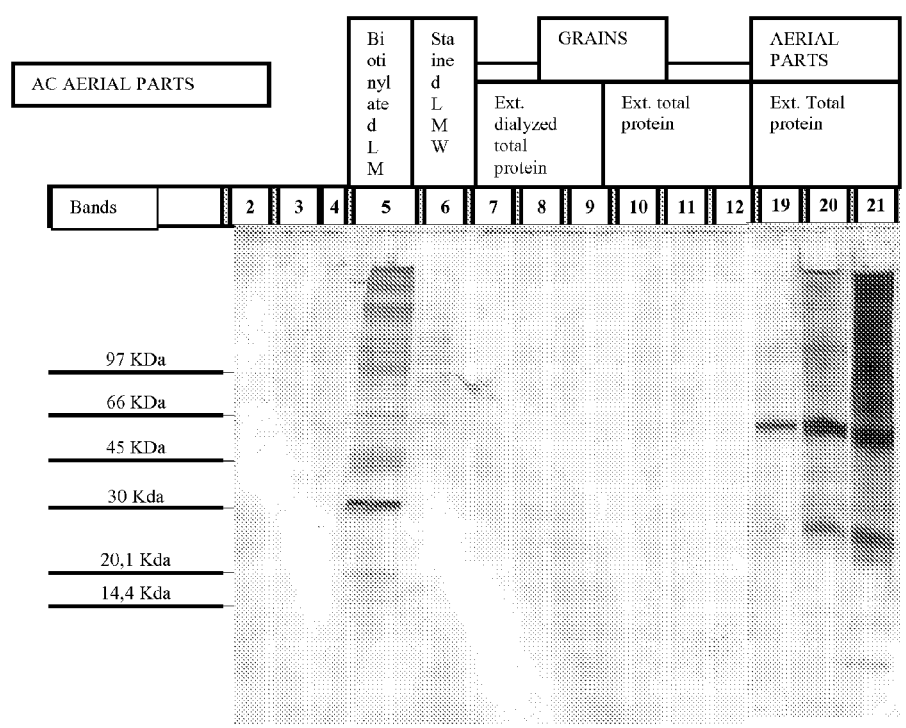

FIG. 2: Western Blot, enzyme staining with anti-aerial part protein polyclonal antibodies.

Figure 3:
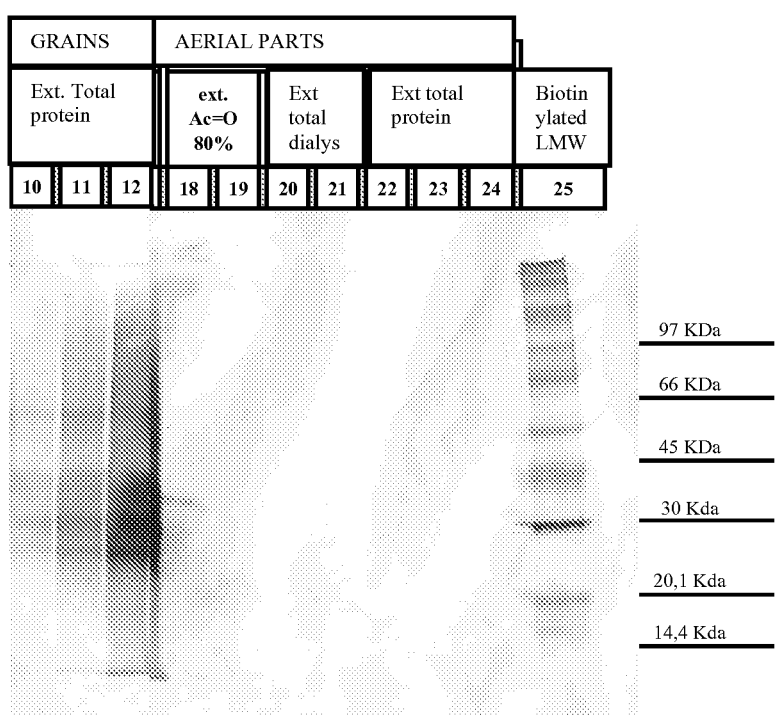

FIG. 3: Western Blot, enzyme staining with anti-grain protein polyclonal antibodies. The following examples are illustrative of, but not limiting to, the invention.

EXAMPLE 1

Preparation of an Extract of Aerial Parts of Oats Harvested Before Ear Emergence by Acetone Extraction 400 kg of dried aerial parts of oats harvested before ear emergence are milled and then placed in a reactor with 10 volumes of acetone/water mixture, under stirring for one hour at room temperature.

A first extraction juice is obtained by solid/liquid separation. The pomace is extracted again with 10 volumes of acetone/water mixture for one hour at room temperature, under stirring. A second extraction juice is obtained by solid/liquid separation and then combined with the first one. The resulting solution is concentrated on water to 1.33 volume/kg and then filtered. The extract thus obtained is dried with microwaves after adding a maltodextrin support (qsp 25%/native extract).

36 kg of a pale brown powder containing 6% flavonoids (isovitexin-2"-O-arabinopyranoside and isoorientin-2"-O-arabinopyranoside) and 0.6% avenacoside B are thus obtained, and the protein content of the extract thus obtained is below 0.3 ppm.

EXAMPLE 2

Biochemical and Immunological Comparison of an Extract of Cereal Grain and an Extract of Aerial Parts of the Same Cereal Harvested Before Ear Emergence The absence of cross-over between extracts of cereal grains and extracts of aerial parts was demonstrated using biochemical (extraction and protein determination) and immunoenzymatic (specific detection of the presence of a protein by means of antibody generation) techniques.

The extract of grain proteins can be prepared as follows:
The grains are milled and extracted with sodium hydroxide at pH 8. After filtration, the filtrate is precipitated by adding hydrochloric acid up to pH 5.4. After centrifugation, the precipitate is taken up, taken into water solution and dialyzed against water in a dialysis bag having a cut-off threshold of 6-8 kDa at 4° C. overnight.

The extract of aerial parts can be prepared as follows:
From fresh material:
  Extraction by solubilization in a Tris.HCl buffer pH 8.0, filtration followed by a series of two precipitations from acetone in order to remove the salts
OR:
  Extraction by solubilization in a reducing Laemmli buffer pH 7.5 containing urea and thiourea, filtration followed by a series of two precipitations from acetone in order to remove the salts
  From dry material:
  Extraction for 27 hours by solubilization in a reducing Laemmli buffer pH 7.5 containing urea and thiourea, filtration followed by a series of two precipitations from acetone in order to remove the salts.

Biochemical and Immunological Study
Biochemical Techniques
I. Electrophoresis
Principle:
The technique for specifically examining proteins is SDS-Page electrophoresis: in the presence of SDS negatively charged proteins migrate in a polyacrylamide gel towards the cathode depending on their mass only, and the proteins are detected by colored stains such as Coomassie blue or silver nitrate.

The positive controls used correspond either to an extract of total proteins of pre-ear emergence aerial parts of oats or an extract of total grain proteins prepared as described above.

II. Illustrative Result—FIG. 1
Comparison of profiles of total grain proteins and pre-ear emergence aerial parts of oats by SDS-Page electrophoresis (12.5% polyacrylamide gel) stained with Coomassie blue.

The electrophoresis profile shown in FIG. 1 reveals a significant difference in protein composition of both extracts tested, especially with regard to the main proteins. However the only way to make sure there is a qualitative difference between these two batches of proteins is to employ immunological techniques, with a specific antigen-antibody recognition.

Immunochemical Techniques
These techniques require first providing antibodies directed against total proteins in aerial parts or grains. For this purpose, extracts of total proteins in aerial parts and grains of one and the same species are administered to rabbits. Polyclonal antibodies are then prepared from the animal sera.

The aim is to demonstrate that the aerial part proteins of pre-ear emergence oats are different from those of grains, and that there is no cross-reaction between grain proteins and aerial part proteins.
  Antibodies directed against aerial part proteins of pre-ear emergence oats versus oat grain proteins
  Antibodies directed against oat grain proteins versus aerial part proteins of pre-ear emergence oats
using ELISA and Western Blot techniques.

I. Direct ELISA
ELISA (Enzyme Linked ImmunoSorbent Assay) is an immunochemical technique for detecting the presence of an antigen in a solution. The principle consists in binding the proteins in the test solution to a well followed by contacting the anti-protein polyclonal antibodies. Then, a second anti-rabbit IgG antibody coupled to an enzyme will reveal, after washing, the presence of antigen in the well using a simple colorimetric reaction.

II. Western Blot
Principle:
The Western Blot technique consists of SDS-Page electrophoresis of a protein mixture followed by staining by a specific antigen-antibody interaction. Only those proteins recognized by the polyclonal antibodies will be revealed: The primary antibodies are then recognized by a secondary antibody (here an anti-rabbit IgG antibody) coupled to an enzyme such as alkaline phosphatase.

Illustrative Result—FIGS. 2 and 3
Cross-over between grain proteins and antibodies directed against the aerial part proteins of pre-ear emergence oats (FIG. 2) and cross-over between aerial part proteins of pre-ear emergence oats and antibodies directed against grain proteins (FIG. 3).

The Western Blot technique confirms the firsts results obtained by ELISA, i.e. that the aerial part proteins of pre-ear emergence oats are different from grain proteins, but also that there is no cross-over between the two.

A patient immunized against oat grain proteins through diet will therefore not react to an aerial part (excluding the grains) extract, even though proteins are contained.

The invention claimed is:
1. A method of reducing allergic reactions to cereal grain proteins in a person allergic to cereal grain proteins, which comprises topically applying to said person allergic to cereal grain proteins a therapeutically effective amount of a composition comprising an acetone extract of aerial part(s) of *avena sativa*, excluding the grain.

* * * * *